US012293513B2

(12) United States Patent
Usher et al.

(10) Patent No.: US 12,293,513 B2
(45) Date of Patent: May 6, 2025

(54) SYSTEMS AND METHODS FOR GENERATING PATIENT-SPECIFIC CORNEAL CROSS-LINKING TREATMENT PATTERNS

(71) Applicant: AVEDRO, INC., Waltham, MA (US)

(72) Inventors: David Usher, Waltham, MA (US); Mikhail Smirnov, North Andover, MA (US); Behrouz Tavakol, Lexington, MA (US); Grace Lytle, Bedford, MA (US)

(73) Assignee: AVEDRO, INC., Burlington, MA (US)

( * ) Notice: Subject to any disclaimer, the term of this patent is extended or adjusted under 35 U.S.C. 154(b) by 268 days.

(21) Appl. No.: 17/689,515

(22) Filed: Mar. 8, 2022

(65) Prior Publication Data

US 2022/0284575 A1 Sep. 8, 2022

Related U.S. Application Data

(60) Provisional application No. 63/158,023, filed on Mar. 8, 2021.

(51) Int. Cl.
*G06T 7/00* (2017.01)
*A61B 3/10* (2006.01)
*A61P 27/02* (2006.01)

(52) U.S. Cl.
CPC ............ *G06T 7/0012* (2013.01); *A61B 3/102* (2013.01); *A61P 27/02* (2018.01); *G06T 2207/10101* (2013.01); *G06T 2207/30041* (2013.01)

(58) Field of Classification Search
CPC ........... A61B 3/102; A61F 2009/00893; A61F 9/0079; A61F 9/008; A61P 27/02;
(Continued)

(56) References Cited

U.S. PATENT DOCUMENTS

| 4,034,750 A | 7/1977 | Seiderman |
| 4,665,913 A | 5/1987 | L'Esperance, Jr. |

(Continued)

FOREIGN PATENT DOCUMENTS

| CN | 110559087 A | 12/2019 |
| DE | 102008046834 | 3/2010 |

(Continued)

OTHER PUBLICATIONS

Ilker et al., "Investigation of the Efficacy of the Cone Location and Magnitude Index in the Diagnosis of Keratoconus", Seminars in Ophthalmology, Early Online, 1-7, 2014 (Year: 2014).*
(Continued)

*Primary Examiner* — Kenny A Cese
(74) *Attorney, Agent, or Firm* — K&L Gates LLP (57) ABSTRACT

An automated process receives input tomography data and generates an optimized (customized) treatment pattern for an individual patient without relying on the physician's analysis and judgment. For example, a method for treating a cornea includes receiving tomographic data for a cornea. The method includes identifying a keratoconic defect in the cornea based on the tomographic data. The method includes segmenting the keratoconic defect into treatment zones based on predefined geometric parameters, wherein the treatment zones indicate where a cross-linking agent is to be applied on the cornea and photoactivated to treat the keratoconic defect.

18 Claims, 6 Drawing Sheets

(58) Field of Classification Search
CPC . G06T 2207/10101; G06T 2207/30041; G06T 7/0012
USPC .................................................. 382/106, 131
See application file for complete search history.

(56) References Cited

U.S. PATENT DOCUMENTS

| | | |
|---|---|---|
| 4,712,543 A | 12/1987 | Baron |
| 4,764,007 A | 8/1988 | Task |
| 4,891,043 A | 1/1990 | Zelmer et al. |
| 4,969,912 A | 11/1990 | Kelman et al. |
| 4,994,058 A | 2/1991 | Raven et al. |
| 5,019,074 A | 5/1991 | Muller |
| 5,171,318 A | 12/1992 | Gibson et al. |
| 5,281,211 A | 1/1994 | Parel et al. |
| 5,332,802 A | 7/1994 | Kelman et al. |
| 5,461,212 A | 10/1995 | Seiler et al. |
| 5,490,849 A | 2/1996 | Smith |
| 5,512,966 A | 4/1996 | Snook |
| 5,562,656 A | 10/1996 | Sumiya |
| 5,624,437 A | 4/1997 | Freeman et al. |
| 5,779,696 A | 7/1998 | Berry et al. |
| 5,786,893 A | 7/1998 | Fink et al. |
| 5,891,131 A | 4/1999 | Rajan et al. |
| 5,910,110 A | 6/1999 | Bastable |
| 6,033,396 A | 3/2000 | Huang et al. |
| 6,139,876 A | 10/2000 | Kolta |
| 6,161,544 A | 12/2000 | DeVore et al. |
| 6,188,500 B1 | 2/2001 | Rudeen et al. |
| 6,218,360 B1 | 4/2001 | Cintron et al. |
| 6,270,221 B1 | 8/2001 | Liang et al. |
| 6,280,436 B1 | 8/2001 | Freeman et al. |
| 6,319,273 B1 | 11/2001 | Chen et al. |
| 6,322,557 B1 | 11/2001 | Nikolaevich et al. |
| 6,325,792 B1 | 12/2001 | Swinger et al. |
| 6,394,999 B1 | 5/2002 | Williams et al. |
| 6,478,792 B1 | 11/2002 | Hansel |
| 6,520,956 B1 | 2/2003 | Huang |
| 6,520,958 B1 | 2/2003 | Shimmick et al. |
| 6,537,545 B1 | 3/2003 | Karageozian et al. |
| 6,571,118 B1 | 5/2003 | Utzinger et al. |
| 6,617,963 B1 | 9/2003 | Watters et al. |
| 6,946,440 B1 | 9/2005 | DeWoolfson et al. |
| 7,001,374 B2 | 2/2006 | Peyman |
| 7,004,902 B2 | 2/2006 | Luce |
| 7,044,945 B2 | 5/2006 | Sand |
| 7,073,510 B2 | 7/2006 | Redmond et al. |
| 7,331,350 B2 | 2/2008 | Kochevar et al. |
| 7,402,562 B2 | 7/2008 | DeWoolfson et al. |
| 7,731,362 B2 | 6/2010 | Gerlach |
| 7,753,943 B2 | 7/2010 | Strong |
| 7,898,656 B2 | 3/2011 | Yun et al. |
| 7,935,058 B2 | 5/2011 | Dupps et al. |
| 8,111,394 B1 | 2/2012 | Borysow et al. |
| 8,115,919 B2 | 2/2012 | Yun et al. |
| 8,366,689 B2 | 2/2013 | Marshall et al. |
| 8,414,911 B2 | 4/2013 | Mattson et al. |
| 8,475,437 B2 | 7/2013 | Mrochen et al. |
| 10,468,142 B1 * | 11/2019 | Abou Shousha ...... G16H 30/20 |
| 2001/0055095 A1 | 12/2001 | D'Souza et al. |
| 2002/0013577 A1 | 1/2002 | Frey et al. |
| 2002/0159618 A1 | 10/2002 | Freeman et al. |
| 2002/0164379 A1 | 11/2002 | Nishihara et al. |
| 2003/0175259 A1 | 9/2003 | Karageozian et al. |
| 2003/0189689 A1 | 10/2003 | Rathjen |
| 2003/0231285 A1 | 12/2003 | Ferguson |
| 2004/0002694 A1 | 1/2004 | Pawlowski et al. |
| 2004/0093046 A1 | 5/2004 | Sand |
| 2004/0199079 A1 | 10/2004 | Chuck et al. |
| 2005/0038471 A1 | 2/2005 | Chan et al. |
| 2005/0096515 A1 | 5/2005 | Geng |
| 2005/0149006 A1 | 7/2005 | Peyman |
| 2005/0271590 A1 | 12/2005 | Schwartz et al. |
| 2006/0135957 A1 | 6/2006 | Panescu |
| 2006/0149343 A1 | 7/2006 | Altshuler et al. |
| 2006/0195076 A1 | 8/2006 | Blumenkranz et al. |
| 2006/0276777 A1 | 12/2006 | Coroneo |
| 2007/0024860 A1 | 2/2007 | Tobiason et al. |
| 2007/0048340 A1 | 3/2007 | Bran et al. |
| 2007/0123845 A1 | 5/2007 | Lubatschowski |
| 2007/0135805 A1 | 6/2007 | Peyman |
| 2007/0142828 A1 | 6/2007 | Peyman |
| 2007/0265603 A1 | 11/2007 | Pinelli |
| 2008/0009901 A1 | 1/2008 | Redmond et al. |
| 2008/0015660 A1 | 1/2008 | Herekar |
| 2008/0063627 A1 | 3/2008 | Stucke et al. |
| 2008/0114283 A1 | 5/2008 | Mattson et al. |
| 2008/0139671 A1 | 6/2008 | Herekar |
| 2008/0208177 A1 | 8/2008 | Mrochen et al. |
| 2009/0116096 A1 | 5/2009 | Zalevsky et al. |
| 2009/0149842 A1 | 6/2009 | Muller et al. |
| 2009/0149923 A1 | 6/2009 | Herekar |
| 2009/0171305 A1 | 7/2009 | El Hage |
| 2009/0234335 A1 | 9/2009 | Yee |
| 2009/0275929 A1 | 11/2009 | Zickler |
| 2010/0028407 A1 | 2/2010 | Del Priore et al. |
| 2010/0057060 A1 | 3/2010 | Herekar |
| 2010/0069894 A1 | 3/2010 | Mrochen et al. |
| 2010/0082018 A1 | 4/2010 | Panthakey et al. |
| 2010/0094197 A1 | 4/2010 | Marshall et al. |
| 2010/0114109 A1 | 5/2010 | Peyman |
| 2010/0149487 A1 | 6/2010 | Ribak |
| 2010/0173019 A1 | 7/2010 | Paik et al. |
| 2010/0189817 A1 | 7/2010 | Krueger et al. |
| 2010/0204584 A1 | 8/2010 | Ornberg et al. |
| 2010/0210996 A1 | 8/2010 | Peyman |
| 2010/0318017 A1 | 12/2010 | Lewis et al. |
| 2011/0077624 A1 | 3/2011 | Brady et al. |
| 2011/0098790 A1 | 4/2011 | Daxer |
| 2011/0118654 A1 | 5/2011 | Muller et al. |
| 2011/0152219 A1 | 6/2011 | Stagni et al. |
| 2011/0190742 A1 | 8/2011 | Anisimov |
| 2011/0202114 A1 | 8/2011 | Kessel et al. |
| 2011/0208300 A1 | 8/2011 | Eugene et al. |
| 2011/0237999 A1 | 9/2011 | Muller et al. |
| 2011/0264082 A1 | 10/2011 | Mrochen |
| 2011/0288466 A1 | 11/2011 | Muller et al. |
| 2011/0301524 A1 | 12/2011 | Bueler et al. |
| 2012/0083772 A1 | 4/2012 | Rubinfield et al. |
| 2012/0215155 A1 | 4/2012 | Muller et al. |
| 2012/0203161 A1 | 8/2012 | Herekar |
| 2012/0289886 A1 | 11/2012 | Muller et al. |
| 2012/0302862 A1 | 11/2012 | Yun et al. |
| 2012/0303008 A1 | 11/2012 | Muller et al. |
| 2012/0310083 A1 | 12/2012 | Friedman et al. |
| 2012/0310223 A1 | 12/2012 | Knox et al. |
| 2013/0060187 A1 | 3/2013 | Friedman et al. |
| 2013/0085370 A1 | 4/2013 | Friedman et al. |
| 2013/0116757 A1 | 5/2013 | Russmann |
| 2014/0113009 A1 * | 4/2014 | Muller ................... A61P 27/10 514/643 |
| 2014/0194957 A1 | 7/2014 | Rubinfield et al. |
| 2014/0249509 A1 | 9/2014 | Rubinfield et al. |
| 2016/0151202 A1 * | 6/2016 | Scarcelli ................ A61F 9/008 606/5 |
| 2016/0364543 A1 * | 12/2016 | Dupps, Jr. .............. G16Z 99/00 |
| 2018/0014725 A1 * | 1/2018 | Bagherinia ............ G06T 7/215 |
| 2018/0193188 A1 * | 7/2018 | Vukelic .................... A61N 1/44 |
| 2018/0206719 A1 * | 7/2018 | Adler ..................... A61B 3/14 |
| 2020/0085617 A1 | 3/2020 | Rajpal et al. |
| 2020/0187771 A1 * | 6/2020 | Yun ..................... A61B 5/0084 |
| 2021/0379397 A1 * | 12/2021 | Epstein ................. A61N 5/062 |

FOREIGN PATENT DOCUMENTS

| | | |
|---|---|---|
| EP | 1561440 | 8/2005 |
| EP | 1790383 | 5/2007 |
| IT | MI2010A001236 | 5/2010 |
| KG | 1376 | 8/2011 |
| RU | 2086215 | 8/1997 |
| RU | 2420330 | 6/2011 |
| RU | 2456971 | 7/2012 |
| WO | 2000074648 | 12/2000 |
| WO | 2001058495 | 8/2001 |

(56) References Cited

FOREIGN PATENT DOCUMENTS

| | | |
|---|---|---|
| WO | 2005110397 | 11/2005 |
| WO | 2006012947 | 2/2006 |
| WO | 2006128038 | 11/2006 |
| WO | 2007001926 | 1/2007 |
| WO | 2007053826 | 5/2007 |
| WO | 2007120457 | 10/2007 |
| WO | 2007139927 | 12/2007 |
| WO | 2007143111 | 12/2007 |
| WO | 2008000478 | 1/2008 |
| WO | 2008052081 | 5/2008 |
| WO | 2008095075 | 8/2008 |
| WO | 2009073213 | 6/2009 |
| WO | 2009114513 | 9/2009 |
| WO | 2009146151 | 12/2009 |
| WO | 2010011119 | 1/2010 |
| WO | 2010015255 | 2/2010 |
| WO | 2010023705 | 3/2010 |
| WO | 2010093908 | 8/2010 |
| WO | 2011019940 | 2/2011 |
| WO | 2011116306 | 9/2011 |
| WO | 2012004726 | 1/2012 |
| WO | 2012149570 | 11/2012 |
| WO | 2012174453 | 12/2012 |
| WO | 2013148713 | 10/2013 |
| WO | 2013148895 | 10/2013 |
| WO | 2013148896 | 10/2013 |
| WO | 2013149075 | 10/2013 |
| WO | 2014202736 | 12/2014 |

OTHER PUBLICATIONS

Rocha K., et al., "Comparative Study of Riboflavin-UVA Cross-linking and "Flash-linking" Using Surface Wave Elastometry," Journal of Refractive Surgery, vol. 24 Issue 7, pp. S748-S751; Sep. 2008 (4 pages).

Rolandi et al. Correlation of Collagen-Linked Fluorescence and Tendon Fiber Breaking Time. Gerontology 1991;27 :240-243 (4 pages).

Scarcelli, G. et al., "Brillouin Optical Microscopy for Corneal Biomechanics", Investigative Ophthalmology & Visual Science, Jan. 2012, vol. 53, No. 1, pp. 185-190 (6 pages).

Sheehan M., et al., "Illumination System for Corneal Collagen Crosslinking," Optometry and Vision Science, vol. 88, No. 4, pp. 512-524; Apr. 2011 (13 pages).

Spoerl E. et al., "Safety of UVA-Riboflavin Cross-Linking of the Cornea," Cornea, vol. 26, No. 4, pp. 385-389; May 2007 (5 pages).

Spoerl E., et al., "Artificial Stiffening of the Cornea by Induction of Intrastromal Cross-links," Oer Ophthalmologe, vol. 94, No. 12, pp. 902-906; Dec. 1997 (5 pages).

Spoerl E., et al., "Induction of Cross-links in Corneal Tissue," Experimental Eye Research, vol. 66, Issue 1, pp. 97-103; Jan. 1998 (7 pages).

Spoerl E., et al., "Techniques for Stiffening the Cornea," Journal of Refractive Surgery, vol. 15, Issue 6, pp. 711-713; Nov.-Dec. 1999 (4 pages).

Tessier FJ, et al., "Rigidification of Corneas Treated in vitro with Glyceraldehyde: Characterization of Two Novel Crosslinks and Two Chromophores," Investigative Opthalmology & Visual Science, vol. 43, E-Abstract; 2002 (2 pages).

Thorton, I. et al., "Biomechancial Effects of Intraocular Pressure Elevation on Optic Berve/Lamina Cribrosa before and after Peripapillary Scleral Collagen Cross-Linking." Invest. Ophthalmol. Vis. Sci., Mar. 2009, 50(3): pp. 1227-1233.

UV-X: Radiation System for Treatment of Keratokonus, Peschke Meditrade GmbH; retrieved from http://www.peschkemed.ch/ on Sep. 27, 2011 (1 page) (date unknown, prior to Sep. 16, 2008).

Vasan S., et al., "An agent cleaving glucose-derived protein crosslinks in vitro and in vivo;" Letters to Nature, vol. 382, pp. 275-278; Jul. 18, 1996 (4 pages).

Verzijl et al. Crosslinking by Advanced Glycation End Products Increases the Stiffness of the Collagen Network in Human Articular Cartilage. Arthritis & Rheumatism vol. 46, No. 1, Jan. 2002, pp. 114-123 (10 pages).

Wollensak G., "Crosslinking Treatment of Progressive Keratoconus: New Hope," Current Opinion in Ophthalmology, vol. 17(4), pp. 356-360; Aug. 2006 (5 pages).

Wollensak G., et al., "Biomechanical and Histological Changes After Corneal Crosslinking With and Without Epithelial Debridement," J. Cataract Refract. Surg., vol. 35, Issue 3, pp. 540-546; Mar. 2009 (7 pages).

Wollensak G., et al., "Collagen Crosslinking of Human and Porcine Sclera," J. Cataract Refract. Surg., vol. 30, Issue 3, pp. 689-695; Mar. 2004 (7 pages).

Wollensak G., et al., "Cross-linking of Scleral Collagen in the Rabbit Using Riboflavin and UVA," Acta Ophtalmologica Scandinavica, vol. 83(4), pp. 477-482; Aug. 2005 (6 pages).

Wollensak G., et al., "Hydration Behavior of Porcine Cornea Crosslinked with Riboflavin and Ultraviolet," A.J. Cataract Refract. Surg., vol. 33, Issue 3, pp. 516-521; Mar. 2007 (6 pages).

Wollensak G., et al., "Riboflavin/Ultraviolet-A-induced Collagen Crosslinking for the Treatment of Keratoconus," American Journal of Ophthalmology, vol. 135, No. 5, pp. 620-627; May 2003 (8 pages).

Wollensak, G. et al. "Laboratory Science: Stress-Strain Measurements of Human and Porcine Corneas after Riboflavin-Ultraviolet-A-Induced Cross-Linking." Journal of Cataract and Refractive Surgery. vol. 29, No. 9, Sep. 2003 (pp. 1780-1785).

Wong, J. et al., "Post-Lasik ectasia: PRK following previous stablization and effective management with Riboflavin I ultraviolet A-induced collagen cross-linking," Association for Research in Vision and Ophthalmology, 2006 (1 page).

Yang H., et al., "3-D Histomorphometry of the Normal and Early Glaucomatous Monkey Optic Nerve Head: Lamina Cribrosa and Peripapillary Scleral Position and Thickness," Investigative Ophthalmology & Visual Science, vol. 48, No. 10, pp. 4597-4607; Oct. 2007 (11 pages).

Yang N., Oster G. Dye-sensitized photopolymerization in the presence of reversible oxygen carriers. J. Phys. Chem. 74, 856-860 (1970).

Zhang, Y. et al., "Effects of Ultraviolet-A and Riboflavin on the Interaction of Collagen and Proteoglycans during Corneal Crosslinking", Journal of Biological Chemistry, vol. 286, No. 15, dated Apr. 5, 2011 (pp. 13011-13022).

Abahussin, M. "3D Collagen Orientation Study of the Human Cornea Using X-ray Diffraction and Femtosecond Laser Technology" Investigative Ophthalmology & Visual Science, Nov. 2009, vol. 50, No. 11, pp. 5159-5164 (6 pages).

Averianova, O. S., "Nastoyaschee I buduschee kross-linkage." Mir Ofalmologii, 2010, [online] [retrieved on Feb. 13, 2014] Retrieved from the internet: http:/ /miroft.org.ualpublications/.html.

Baier J. et al., "Singlet Oxygen Generation by UVA Light Exposure of Endogenous Photosensitizers," Biophysical Journal, vol. 91(4), pp. 1452-1459; Aug. 15, 2006 (8 pages).

Ballou, D. et al., "Direct Demonstration Of Superoxide Anion Production During The Oxidation Of Reduced Flavin And Of Its Catalytic Decomposition By Erythrocuprein," Biochemical And Biophysical Research Communications vol. 36, No. 6, pp. 898-904, Jul. 11, 1969 (7 pages).

Barbarino, S. et al., "Post-LASIK ectasia: Stabilization and Effective Managmeent with Riboflavin / ultraviolet A-induced collagen cross-linking," Association for Research in Vision and Ophthalmology, 2006 (1 page).

Bruel, A., "Changes In Biomechanical Properties, Composition Of Collagen And Elastin, And Advanced Glycation Endproducts Of The Rat Aorta In Relation To Age," Atherosclerosis 127, Mar. 14, 1996 (11 pages).

Chace, K.V. et al., Abstract for "The role of nonenzymatic glycosylation, transition metals, and free radicals in the formation of collagen aggregates", Arch Biochem Biophys., Aug. 1, 1991, 288(2) pp. 473-480 (1 page).

(56) References Cited

OTHER PUBLICATIONS

Chai, D. et al., "Quantitative Assessment of UVA-Riboflavin Corneal Cross-Linking Using Nonlinear Optical Microscopy," Investigative Ophthalmology & Visual Science, Jun. 2011, vol. 52, No. 7, 4231-4238 (8 pages).
Chan B.P., et al., "Effects of photochemical crosslinking on the microstructure of collagen and a feasibility study on controlled protein release;" Acta Biomaterialia, vol. 4, Issue 6, pp. 1627-1636; Jul. 1, 2008 (10 pages).
Clinical Trials.gov, "Riboflavin Mediated Corneal Crosslinking for Stabilizing Progression of Keratoconus (CCL)," University Hospital Freiburg, Feb. 20, 2008; retrieved from http://www.clinicaltrials.gov/ct2/show/NCT00626717, on Apr. 26, 2011 (3 pages).
Coskenseven E. et al., "Comparative Study of Corneal Collagen Cross-linking With Riboflaving and UVA Irradiation in Patients With Keratoconus," Journal of Refractive Surgery, vol. 25, issue 4, pp. 371-376; Apr. 2009 (6 pages).
Erskine H., "Avedro Becomes Sponsor of US FDA Clinical Trials of Corneal Collagen Crosslinking," Press Release, Mar. 16, 2010 (1 page).
Fite et al. Noninvasive Multimodal Evaluation of Bioengineered Cartilage Constructs Combining Time-Resolved Fluorescence and Ultrasound Imaging. Tissue Eng: Part C vol. 17, No. 4, 2011 (10 pages).
Friedman, M. et al. "Advanced Corneal Cross-Linking System with Fluorescence Dosimetry", Journal of Ophthalmology, vol. 2012, Article ID 303459, dated May 7, 2012 (6 pages).
Gibson, Q. et al., "The Oxidation Of Reduced Flavin Mononucleotide By Molecular Oxygen," Biochem. J. (1962) 83, 368-377 (10 pages).
Givens et al. "A Photoactivated Diazpryruvoyl Cross-Linking Agent for Bonding Tissue Containing Type-I Collagen." Photochemistry and Photobiology. vol. 78, No. 1, 2003 (pp. 23-29).
Glenn J.V., et al., "Advanced Glycation End Product (AGE) Accumulation on Bruch's Membrane: Links to Age-Related RPE Dysfunction;" Investigative Ophthalmology & Visual Science, vol. 50, No. 1, pp. 441-451; Jan. 2009 (11 pages).
Hafezi F., et al., "Collagen Crosslinking with Ultraviolet-A and Hypoosmolar Riboflavin Solution in Thin Corneas," J. Catract Refract. Surg., vol. 35, No. 1, pp. 621-624; Apr. 2009 (4 pages).
Hitzenberger et al., "Birefringence Properties Of The Human Cornea Measured With Polarization Sensitive Optical Coherence Tomography," Bull. Soc. Beige Ophtalmol., 302, 153-168, 2006.
Holmstrom, B. et al., "Riboflavin As An Electron Donor In Photochemical Reactions," 1867-1871, Nov. 29, 1960 (5 pages).
Imex, "KXL System: Crosslinking Para Cirugia Corneal Bibliografia Cientifica," Product Literature, Nov. 23, 2010 (24 pages).
Kamaev et al., "Photochemical Kinetics Of Corneal Cross-Linking With Riboflavin," Investigative Ophthalmology & Visual Science, Apr. 2012, vol. 53, No. 4, pp. 2360-2367 (8 pages).
Kampik D. et al., "Influence of Corneal Collagen Crosslinking With Riboflavin and Ultraviolet-A Irradiation on Excimer Laser Surgery," Investigative Opthalmology & Visual Science, vol. 51, No. 8, pp. 3929-3934; Aug. 2010 (6 pages).
Kanellopoulos, A. J., "Collagen Cross-linking in Early Keratoconus With Riboflavin in a Femtosecond Laser-created Pocket: Initial Clinical Results", Journal of Refractive Surgery, Aug. 18, 2009.
Kanellopoulos, A. J., "Keratoconus management: UV A-induced collagen cross-linking followed by a limited topo-guided surface excimer ablation," American Academy of Ophthalmology, 2006 (25 pages).
Kanellopoulos, A. J., "Ultraviolet A cornea collagen cross-linking, as a pre-treatment for surface excimer ablation in the management of keratoconus and post-LASIK ectasia," American Academy of Ophthalmology, 2005 (28 pages).
Kissner Anja, et al., "Pharmacological Modification of the Epithelial Permeability by Benzalkonium Chloride in UVNRiboflavin Corneal Collagen Cross-Linking," Current Eye Research 35(8), pp. 715-721; Mar. 2010 (7 pages).
Koller T., et al., "Therapeutische Quervernetzung der Hornhaut mittels UVA und Riboflavin: Therapeutic Cross-Linking of the Cornea Using Riboflavin/UVA," Klinische Monatsblatter fur Augenheilkunde, val. 224, No. 9, pp. 700-706; Sep. 2007 (7 pages).
Koller, T. et al., "Complication and failure rates after corneal crosslinking," Journal Cataract and refractive surgery, vol. 35, No. 8, Aug. 2009, pp. 1358-1362.
Kornilovsky, I. M. "Novye neinvazivnye tekhnologii lazernoy modifikatsii optiko-refraksionnykk struktur glaza. Refraktsionnaya khirurgiya I oftalmologiya." vol. 9, No. 3, 2006 (pts. 17-26).
Krueger Ronald R., "Rapid VS Standard Collagen CXL with Equivalent Energy Dosing," presentation slides, (26 pages); available at http://www.slideshare.net/logen/krueger-kerekar-rapid-cross-linking (date unknown, prior to Nov. 9, 2009).
Li, C. et al. "Elastic Properties of Soft Tissue-Mimicking Phantoms Assessed by Combined Use of Laser Ultrasonics and Low Coherence Interferometry." Optics Express. vol. 19, No. 11, May 9, 2011 (pp. 10153-10163).
Li, C. et al. "Noncontact All-Optical Measurement of Corneal Elasticity." Optics Letters. vol. 37, No. 10, May 15, 2012 (pp. 1625-1627).
Li, P. et al. "In Vivo Microstructural and Microvascular Imaging of the Human Corneo-Scleral Limbus Using Optical Coherence Tomography." Biomedical Optics Express. vol. 2, No. 11, Oct. 18, 2011 (pp. 3109-3118).
Marzouky, et. al., Tensioactive-mediated Transepithelial Corneal Cross-linking—First Laboratory Report, European Ophthalmic Review, 2009, 3(2), pp. 67-70.
Massey, V., "Activation Of Molecular Oxygen By Flavins And Flavoproteins," The Journal of Biological Chemistry vol. 269, No. 36, Issue of Sep. 9, pp. 22459-22462, 1994 (4 pages).
Meek, K.M. et al. "The Cornea and Sclera", Collagen: Structure and Mechanics, Chapter 13, pp. 359-396, 2008 (38 pages).
Mi S., et al., "The adhesion of LASIK-like flaps in the cornea: effects of cross-linking, stromal fibroblasts and cytokine treatment," presented at British Society for Matrix Biology annual Meeting, Cardiff, UK, Sep. 8-9, 2008 (17 pages).
Muller L., et al., "The Specific Architecture of the Anterior Stroma Accounts for Maintenance of Corneal Curvature," Br. J. Opthalmol., vol. 85, pp. 437-443; Apr. 2001 (8 pages).
Mulroy L., et al., "Photochemical Keratodesmos for repair of Lamellar corneal Incisions;" Investigative Ophthalmology & Visual Science, vol. 41, No. 11, pp. 3335-3340; Oct. 2000 (6 pages).
O'Neil A.C., et al., "Microvascular Anastomosis Using a Photochemical Tissue Bonding Technique;" Lasers in Surgery and Medicine, vol. 39, Issue 9, pp. 716-722; Oct. 2007 (7 pages).
Pinelli R., et al., "C3-Riboflaving Treatments: Where Did We Come From? Where Are We Now?" Cataract & Refractive Surgery Today Europe, Summer 2007, pp. 36-46; Jun. 2007 (10 pages).
Pinelli, R. "Corneal Cross-Linking with Riboflavin: Entering a New Era in Ophthalmology." Ophthalmology Times Europe. vol. 2, No. 7, Sep. 1, 2006 (3 pages).
Pinelli, R., "Panel Discussion: Epithelium On/Off, Corneal abrasion for CCL contra", presented at the 3° International Congress of Corneal Cross Linking on Dec. 7-8, 2007 in Zurich (36 pages).
Ponce C., et al., "Central and Peripheral Corneal Thickness Measured with Optical Coherence Tomography, Scheimpflug Imaging, and Ultrasound Pachymetry in Normal, Keratoconus-suspect and Post-laser in situ Keratomileusis Eyes," J. Cataract Refract. Surgery, vol. 35, No. 6, pp. 1055-1062; Jun. 2009 (8 pages).
Proano C.E., et al., "Photochemical Keratodesmos for Bonding Corneal Incisions;" Investigative Ophthalmology & Visual Science, vol. 45, No. 7, pp. 2177-2181; Jul. 2004 (5 pages).
Randall, J. et al., "The Measurement and Intrepretation of Brillouin Scattering in the Lens of the Eye," The Royal Society, Abstract only, published 2013 [available online at http://rspb.royalsocietypublishing.org/content/214/11971449.short] (1 page).
Reinstein, D. Z. et al. "Epithelial Thickness Profile as a Method to Evaluate the Effectiveness of Collagen Cross-Linking Treatment After Corneal Ectasis." Journal of Refractive Surgery. vol. 27, No. 5, May 2011 (pp. 356-363). [Abstract only].
Reiss, S. et al., "Non-Invasive, ortsaufgeloeste Bestimmung von Gewebeeigenschaften der Augenlinse, Dichte undProteinkonzentra- (56) References Cited

OTHER PUBLICATIONS tion unter Anwendung der Brillouin-spektroskopie", Klin Monatsbl Augenheilkd, vol. 228, No. 12, pp. 1079-1085, Dec. 13, 2011 (7 pages).

Reiss, S. et al., "Spatially resolved Brillouin Spectroscopy to determine the rheological properties of the eye lens", Biomedical Optics Express, vol. 2, No. 8, p. 2144, Aug. 1, 2011 (1 page).

International Search Report and Written Opinion for related International Application No. PCT/US2022/019314; action dated Jun. 15, 2022; (33 page).

* cited by examiner

SYSTEMS AND METHODS FOR GENERATING PATIENT-SPECIFIC CORNEAL CROSS-LINKING TREATMENT PATTERNS

CROSS-REFERENCE TO RELATED APPLICATIONS

This application claims priority to U.S. Provisional Patent Application No. 63/158,023, filed Mar. 8, 2021, the contents of which are incorporated entirely herein by reference.

BACKGROUND

Field

The present disclosure pertains to systems and methods for eye treatments, and more particularly, to systems and methods for conical cross-linking treatments.

Description of Related Art

Cross-linking treatments may be employed to treat eyes suffering from disorders, such as keratoconus. In particular, keratoconus is a degenerative disorder of the eye in which structural changes within the cornea cause it to weaken and change to an abnormal conical shape. Cross-linking treatments can strengthen and stabilize areas weakened by keratoconus and prevent disease progression.

SUMMARY

According to aspects of the present disclosure, an automated process receives input tomography data and generates an optimized (customized) treatment pattern for an individual patient without relying on the physician's analysis and judgment.

For example, a method for treating a cornea includes receiving tomographic data for a cornea. The method includes identifying a keratoconic defect in the cornea based on the tomographic data. The method includes segmenting the keratoconic defect into treatment zones based on pre-defined geometric parameters, wherein the treatment zones indicate where a cross-linking agent is to be applied on the cornea and photoactivated to treat the keratoconic defect.

For example, a system for treating a cornea, includes an illumination system configured to deliver illumination that activates a photosensitizing agent applied to a cornea. The system includes a controller configured to control the illumination system. The controller includes one or more processors and one or more computer readable media, the one or more processors configured to execute instructions from the computer readable media to cause the controller to: receive tomographic data for a cornea; identify a keratoconic defect in the cornea based on the tomographic data; segment the keratoconic defect into treatment zones based on pre-defined geometric parameters, wherein the treatment zones indicate where a cross-linking agent is to be applied on the cornea and photoactivated to treat the keratoconic defect; and cause the illumination system to deliver the illumination to photoactivate the cross-linking agent according to the treatment zones.

BRIEF DESCRIPTION OF THE DRAWINGS

FIG. 3D illustrates example segmentation (without the post-processing) based on a pachymetry topography map as input.

FIGS. 6A-D illustrate examples of segmentation produced by act 230*h* with the post-processing of act 230*c*, where the maximum eccentricity is bounded to 0.606.

FIG. GD illustrates example segmentation (with post-processing specifying maximum eccentricity) based on a pachymetry topography map as input.

While the present disclosure is susceptible to various modifications and alternative forms, a specific embodiment thereof has been shown by way of example in the drawings and will herein be described in detail. It should be understood, however, that it is not intended to limit the present disclosure to the particular forms disclosed, but on the contrary, the intention is to cover all modifications, equivalents, and alternatives falling within the spirit of the present disclosure.

DESCRIPTION

Figure 1:
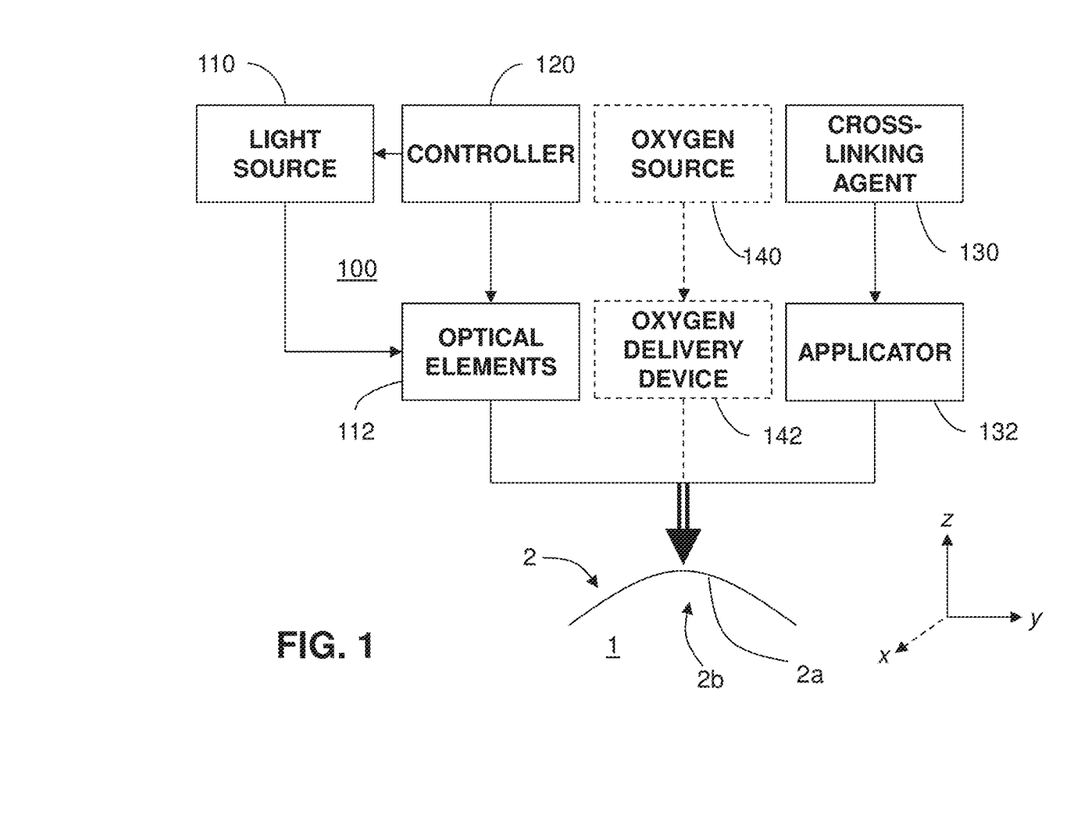
FIG. 1 illustrates an example system that delivers a cross-linking agent and photoactivating light to a cornea of an eye in order to generate cross-linking of corneal collagen, according to aspects of the present disclosure.

FIG. 1 illustrates an example treatment system 100 for generating cross-linking of collagen in a cornea 2 of an eye 1. The treatment system 100 includes an applicator 132 for applying a cross-linking agent 130 to the cornea 2. In example embodiments, the applicator 132 may be an eye dropper, syringe, or the like that applies the photosensitizer 130 as drops to the cornea 2. Example systems and methods for applying the cross-linking agent are described in U.S. Patent Application Publication No. 2017/0296383, filed Apr.

13, 2017 and titled "Systems and Methods for Delivering Drugs to an Eye," the contents of which are incorporated entirely herein by reference.

The cross-linking agent 130 may be provided in a formulation that allows the cross-linking agent 130 to pass through the corneal epithelium 2a and to underlying regions in the conical stroma 2b (also known as an "epi-on" procedure). Alternatively, the conical epithelium. 2a may be removed or otherwise incised to allow the cross-linking agent 130 to be applied more directly to the underlying tissue (also known as an "epi-off" procedure).

The treatment system 100 includes an illumination system with a light source 110 and optical elements 112 for directing light to the cornea 2. In some embodiments, the light source 110 may include a light emitting diode (LED). In other embodiments, the light source 110 may provide a laser. The light causes photoactivation of the cross-linking agent 130 to generate cross-linking activity in the cornea 2. For example, the cross-linking agent may include riboflavin and the photoactivating light may include ultraviolet A (UVA) (e.g., approximately 365 nm or 375 nm, or a wavelength falling within the band of 315 nm to 400 nm) light. Alternatively, the photoactivating light may include another wavelength, such as a visible wavelength (e.g., approximately 452 nm) or any other wavelength selected to activate a photosensitizing agent. As described further below, corneal cross-linking improves conical strength by creating chemical bonds within the corneal tissue according to a system of photochemical kinetic reactions.

Riboflavin and the photoactivating light may be applied to stabilize and/or strengthen conical tissue to address corneal ectatic disorders, such as keratoconus or post-LASIK ectasia. The application of riboflavin and the photoactivating light may also allow for various amounts of refractive correction, which for instance, may involve combinations of myopia, hyperopia, astigmatism, irregular astigmatism, presbyopia and complex corneal refractive surface corrections due to conical ectatic disorders as well as other conditions of corneal biomechanical alteration/degeneration, etc.

The treatment system 100 includes one or more controllers 120 that control aspects of the treatment system 100, including the light source 110 and/or the optical elements 112. In an implementation, the cornea 2 can be more broadly treated with the cross-linking agent 130 (e.g., with an eye dropper, syringe, etc), and the photoactivating light from the light source 110 can be selectively directed to regions of the treated cornea 2 according to a particular pattern.

The optical elements 112 may include one or more mirrors, lenses, or other optical components for directing and focusing the photoactivating light emitted by the light source 110 to a particular pattern on the cornea 2. The optical elements 112 may further include filters for partially blocking wavelengths of light emitted by the light source 110 and for selecting particular wavelengths of light to be directed to the cornea 2 for photoactivating the cross-linking agent 130. In addition, the optical elements 112 may include one or more beam splitters for dividing a beam of light emitted by the light source 110, and may include one or more optical sinks for absorbing light emitted by the light source 110. The optical elements 112 may also accurately and precisely focus the photo-activating light to particular focal planes within the cornea 2, e.g., at a particular depths in the underlying region 2b where cross-linking activity is desired.

According to some aspects, optical elements of an example treatment system may employ fiber-optic elements. The use of fiber-optic elements can eliminate the need for free space optical elements as well as opto-mechanical mounts in a treatment system. Advantageously, the use of fiber-optics can reduce the size and footprint of a treatment system, reduce design and manufacturing complexity and cost, and enhance reliability.

Moreover, specific regimes of the photoactivating light can be modulated to achieve a desired degree of cross-linking in the selected regions of the cornea 2. The one or more controllers 120 may be used to control the operation of the light source 110 and/or the optical elements 112 to precisely deliver the photoactivating light according to any combination of wavelength, bandwidth, intensity, power, location, depth of penetration, and/or duration of treatment (the duration of the exposure cycle, the dark cycle, and the ratio of the exposure cycle to the dark cycle duration).

The parameters for photoactivation of the cross-linking agent 130 can be adjusted, for example, to reduce the amount of time required to achieve the desired cross-linking, in an example implementation, the time can be reduced from minutes to seconds. While some configurations may apply the photoactivating light at an irradiance of 5 mW/cm$^2$, larger irradiance of the photoactivating light, e.g., multiples of 5 mW/cm$^2$, can be applied to reduce the time required to achieve the desired cross-linking. The total dose of energy absorbed in the cornea 2 can be described as an effective dose, which is an amount of energy absorbed through an area of the corneal epithelium 2a. For example the effective dose for a region of the cortical surface 2A can be, for example, 5 μcm$^2$, or as high as 20 μcm$^2$ or 30 J/cm$^2$. The effective dose described can be delivered from a single application of energy, or from repeated applications of energy.

The optical elements 112 of the treatment system 100 may include a microelectromechanical system (MEMS) device, e.g., a digital micro-mirror device (DMD), to modulate the application of photoactivating light spatially and temporally. Using DMD technology, the photoactivating light from the light source 110, e.g., an LED, is projected in a precise spatial pattern that is created by microscopically small mirrors laid out in an array on a semiconductor chip. Each mirror represents one or more pixels in the pattern of projected light. With the DMD one can perform topography guided cross-linking. The control of the DMD according to topography may employ several different spatial and temporal irradiance and dose profiles. These spatial and temporal dose profiles may be created using continuous wave illumination but may also be modulated via pulsed illumination by pulsing the illumination source under varying frequency and duty cycle regimes. Alternatively, the DMD can modulate different frequencies and duty cycles on a pixel by pixel basis to give ultimate flexibility using continuous wave illumination. Or alternatively, both pulsed illumination and modulated DMD frequency and duty cycle combinations may be combined. This allows for specific amounts of spatially determined conical cross-linking. This spatially determined cross-linking may be combined with dosimetry, interferometry, optical coherence tomography (OCT), corneal topography, etc., for pre-treatment planning and/or real time monitoring and modulation of conical cross-linking during treatment. Additionally, pre-clinical patient information may be combined with finite element biomechanical computer modeling to create patient specific pre-treatment plans.

To control aspects of the delivery of the photoactivating light, embodiments may also employ aspects of muitiphoton excitation microscopy. In particular, rather than delivering a single photon of a particular wavelength to the cornea 2, the treatment system 100 may deliver multiple photons of longer wavelengths, i.e., lower energy, that combine to initiate the cross-linking. Advantageously, longer wavelengths are scattered within the cornea 2 to a lesser degree than shorter wavelengths, which allows longer wavelengths of light to penetrate the cornea 2 more efficiently than light of shorter wavelengths. Shielding effects of incident irradiation at deeper depths within the cornea are also reduced over conventional short wavelength illumination since the absorption of the light by the photosensitizer is much less at the longer wavelengths. This allows for enhanced control over depth specific cross-linking. For example, in some embodiments, two photons may be employed, where each photon carries approximately half the energy necessary to excite the molecules in the cross-linking agent 130 to generate the photochemical kinetic reactions described further below. When a cross-linking agent molecule simultaneously absorbs both photons, it absorbs enough energy to release reactive radicals in the corneal tissue. Embodiments may also utilize lower energy photons such that a cross-linking agent molecule must simultaneously absorb, for example, three, four, or five, photons to release a reactive radical. The probability of the near-simultaneous absorption of multiple photons is low, so a high flux of excitation photons may be required, and the high flux may be delivered through a femtosecond laser.

A large number of conditions and parameters affect the cross-linking of corneal collagen with the cross-linking agent 130. For example, the irradiance and the dose of photoactivating light affect the amount and the rate of cross-linking.

When the cross-linking agent 130 is riboflavin in particular, the INA light may be applied continuously (continuous wave (CW)) or as pulsed light, and this selection has an effect on the amount, the rate, and the extent of cross-linking. If the INA light is applied as pulsed light, the duration of the exposure cycle, the dark cycle, and the ratio of the exposure cycle to the dark cycle duration have an effect on the resulting corneal stiffening. Pulsed light illumination can be used to create greater or lesser stiffening of corneal tissue than may be achieved with continuous wave illumination for the same amount or dose of energy delivered. Light pulses of suitable length and frequency may be used to achieve more optimal chemical amplification. For pulsed light treatment, the on/off duty cycle may be between approximately 1000/1 to approximately 1/1000 the irradiance may be between approximately 1 $mW/cm^2$ to approximately 1000 $mW/cm^2$ average irradiance, and the pulse rate may be between approximately 0.01 HZ to approximately 1000 Hz or between approximately 1000 Hz to approximately 100,000 Hz.

The treatment system 100 may generate pulsed light by employing a DMD, electronically turning the light source 110 on and off, and/or using a mechanical or opto-electronic (e.g., Pockets cells) shutter or mechanical chopper or rotating aperture. Because of the pixel specific modulation capabilities of the DMD and the subsequent stiffness impartment based on the modulated frequency, duty cycle, irradiance and dose delivered to the cornea, complex biomechanical stiffness patterns may be imparted to the cornea. A specific advantage of the DMD system and method is that it allows for randomized asynchronous pulsed topographic patterning, creating a non-periodic and uniformly appearing illumination which eliminates the possibility for triggering photosensitive epileptic seizures or flicker vertigo for pulsed frequencies between 2 Hz and 84 Hz.

Although example embodiments may employ stepwise on/off pulsed light functions, it is understood that other functions for applying light to the cornea may be employed to achieve similar effects. For example, light may be applied to the cornea according to a sinusoidal function, sawtooth function, or other complex functions or curves, or any combination of functions or curves. Indeed, it is understood that the function may be substantially stepwise where there may be more gradual transitions between on/off values. In addition, it is understood that irradiance does not have to decrease down to a value of zero during the off cycle, and may be above zero during the off cycle. Desired effects may be achieved by applying light to the cornea according to a curve varying irradiance between two or more values.

Examples of systems and methods for delivering photoactivating light are described, for example, in U.S. Patent Application Publication No. 2011/0237999, filed Mar. 18, 2011 and titled "Systems and Methods for Applying and Monitoring Eye Therapy," U.S. Patent Application Publication No. 2012/0215155, filed Apr. 3, 2012 and titled "Systems and Methods for Applying and Monitoring Eye Therapy," and U.S. Patent Application Publication No. 2013/0245536, filed Mar. 15, 2013 and titled "Systems and Methods for Corneal Cross-Linking with Pulsed Light," the contents of these applications being incorporated entirely herein by reference. Embodiments may generate cross-linking activity in the cornea according to circular and/or annular patterns defined by the delivery of photoactivating light (e.g., via the DMD described above). Additionally or alternatively, embodiments may generate cross-linking activity in the cornea according to non-circular and/or non-annular patterns defined by the delivery of photoactivating light (e.g., via the DMD).

Patterns of photoactivating light can be applied (e.g., via the DMD) to the eye in separate treatment zones with different doses sequentially or continuously applied. For instance, one treatment zone can be "turned off" (i.e., delivery of the corresponding photoactivating light ceases) while another "stays on" (i.e., delivery of the corresponding photoactivating light continues). The treatment zones can be, for instance, annularly shaped about a center point of the eye. There may also be discontinuous zones where no the photoactivating light is applied (e.g., a central treatment zone surrounded by an annulus of no light surrounded by an annular treatment zone of light, etc.). The widths of the annular zones can be of different dimensions, e.g., one annular zone has a width of 1 mm and another has a width of 2 mm. Applying the photoactivating light in annular treatment zones on the periphery of the eye without a central treatment zone can result in a hyperopic correction, for instance, by causing the central region of the eye to have an increased curvature while the periphery is strengthened. In some cases, central and surrounding treatment zones can be elliptical in shape, for instance to address astigmatism, by preferentially generating cross-linking activity in regions of the cornea to correct the astigmatism. Such elliptically shaped annular treatment zones are preferentially oriented with the axis of the annular treatment zones aligned according to the orientation of the astigmatism. The elliptically shaped treatment zones can also be irregularly asymmetric (i.e., having major and minor axis that are not perpendicular and can be situated with distinct center points (centers of mass)).

Cross-linking treatments can be tuned according to one or more biomechanical properties of the eye, such as the conical topography (i.e., shape), corneal strength (i.e., stiffness), and/or corneal thickness. Optical correction and/or strengthening of the cornea can be achieved by applying the cross-linking agent and/or photoactivating light in one or more iterations with adjustable characteristics for each iteration. Generally, a developed treatment plan can include a number of applications of the cross-linking agent, the amount and concentration of the cross-linking agent for each application, the number of applications of photoactivating light, and the timing, duration, power, energy dosage, and pattern of the photoactivating light for each application. Furthermore, the cross-linking treatments can be adapted based on feedback information relating to the biomechanical properties gathered in real time during treatment or during breaks in treatments.

The addition of oxygen also affects the amount of corneal cross-linking. In human tissue, $O_2$ content is very low compared to the atmosphere. The rate of cross-linking in the cornea, however, is related to the concentration of $O_2$ when it is irradiated with photoactivating light. Therefore, it may be advantageous to increase or decrease the concentration of $O_2$ actively during irradiation to control the rate of cross-linking until a desired amount of cross-linking is achieved. Oxygen may be applied during the cross-linking treatments in a number of different ways. One approach involves supersaturating the riboflavin with $O_2$. Thus, when the riboflavin is applied to the eye, a higher concentration of $O_2$ is delivered directly into the cornea with the riboflavin and affects the reactions involving $O_2$ when the riboflavin is exposed to the photoactivating light. According to another approach, a steady state of $O_2$ (at a selected concentration) may be maintained at the surface of the cornea to expose the cornea to a selected amount of $O_2$ and cause $O_2$ to enter the cornea. As shown in FIG. 1, for instance, the treatment system 100 also includes an oxygen source 140 and an oxygen delivery device 142 that optionally delivers oxygen at a selected concentration to the cornea 2. Example systems and methods for applying oxygen during cross-linking treatments are described, for example, in U.S. Pat. No. 8,574,277, filed Oct. 21, 2010 and titled "Eye Therapy," U.S. Patent Application Publication No. 2013/0060187, filed Oct. 31, 2012 and titled "Systems and Methods for Corneal Cross-Linking with Pulsed Light," the contents of these applications being incorporated entirely herein by reference. Additionally, an example mask device for delivering concentrations of oxygen as well as photoactivating light in eye treatments is described in U.S. Patent Application Publication No. 2017/0156926, filed Dec. 3, 2016 and titled "Systems and Methods for Treating an Eye with a Mask Device," the contents of which are incorporated entirely herein by reference. For instance, a mask may be placed over the eye(s) to produce a consistent and known oxygen concentration above the surface.

When riboflavin absorbs radiant energy, especially light, it undergoes photoactivation. There are two photochemical kinetic pathways for riboflavin photoactivation, Type I and Type II. The reactions involved in both the Type I and Type II mechanisms and other aspects of the photochemical kinetic reactions generating cross-linking activity are described in U.S. Patent Application Publication No. 2016/0310319, filed Apr. 27, 2016 and titled "Systems and Methods for Cross-Linking Treatments of an Eye," the contents of which are incorporated entirely herein by reference.

As described above, the treatment system 100 includes optical elements 112 that direct light (e.g., UV light) from a light source 110 to photoactivate the cross-linking agent 130 (e.g., riboflavin) applied to the cornea 2 and thus generate cross-linking activity. In particular, the photoactivating light can be selectively directed to regions of the cornea 2 according to a particular spatial treatment pattern. In some embodiments, a treatment system can provide an adjustable treatment pattern so that different ophthalmic conditions can be treated with the same treatment system.

Example treatment systems that treat different ophthalmic conditions by providing different treatment patterns are described in U.S. Patent Application Publication No. 2020/0107953, filed Oct. 9, 2019 and titled "Photoactivation Systems and Methods for Corneal Cross-Linking Treatments," the contents of which are incorporated entirely herein by reference.

To treat patients with keratoconus, cross-linking treatments strengthen and stabilize the cornea and prevent disease progression. Providing a cross-linking treatment that also restores visual quality also represents a significant improvement for these patients. Restoring visual quality involves reduction of visual aberrations and regularization of the corneal surface, which can be achieved by customizing the treatment pattern (e.g., pattern of UV light) to the specific morphology of the cornea of each individual patient. According to aspects of the present disclosure, an automated process receives input tomography data and generates an optimized (customized) treatment pattern for an individual patient without relying on the physician's analysis and judgment. Advantageously, this process reduces the burden on physicians and also reduces subjectivity in determination of treatment patterns. In some cases, the one or more controllers 120 described above may implement the automated process and aspects of the treatment system 100, e.g., the light source 110 and the optical elements 112, can deliver the optimized treatment pattern to the cornea 2 as a part of a treatment plan.

Figure 2:
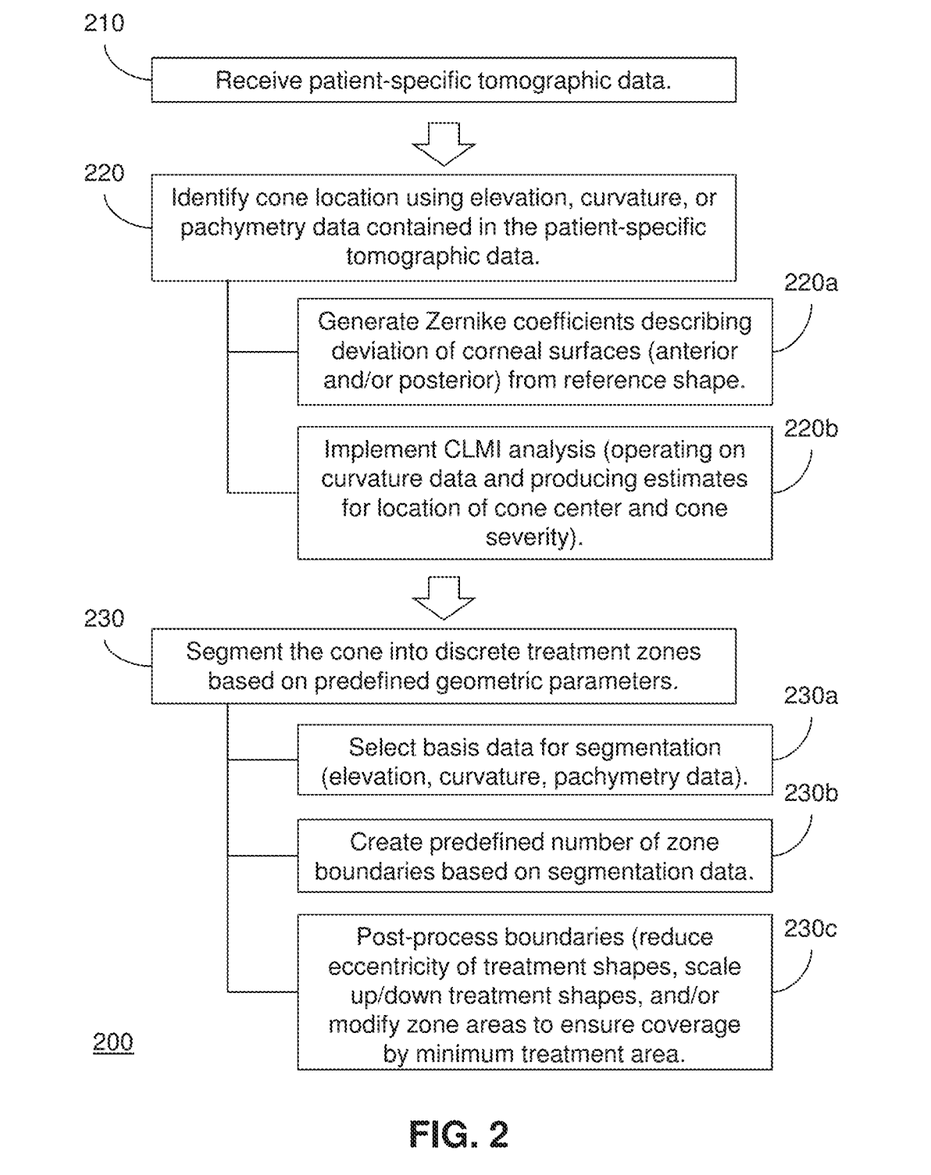
FIG. 2 illustrates an example automated process for generating optimized treatment patterns for eyes with keratoconus.
Figure 3A:
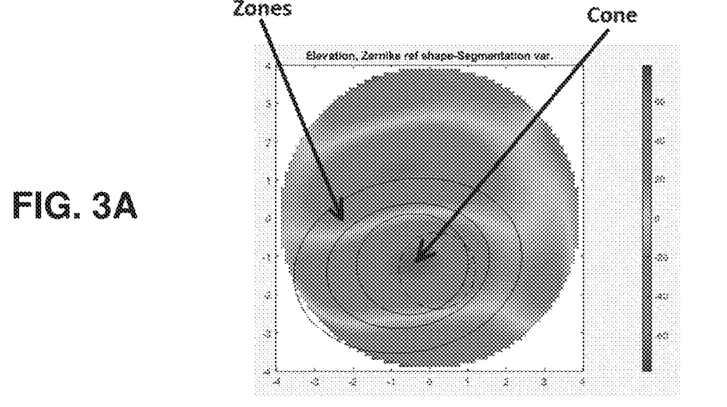
FIG. 3A illustrates an example topography map showing elevation float (relative to reference shape of low order Zernike polynomials)
Figure 3B:
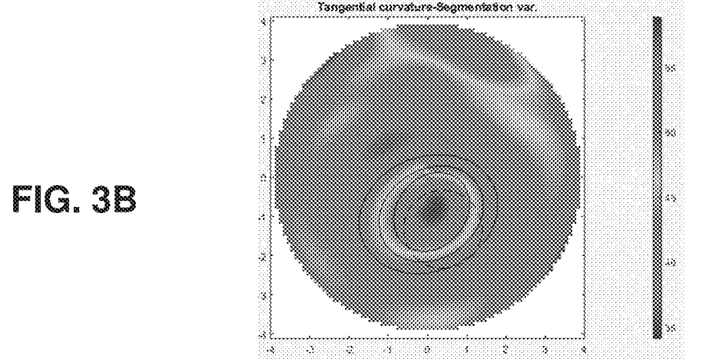
FIG. 3B illustrates an example topography map showing tangential curvature.
Figure 3C:
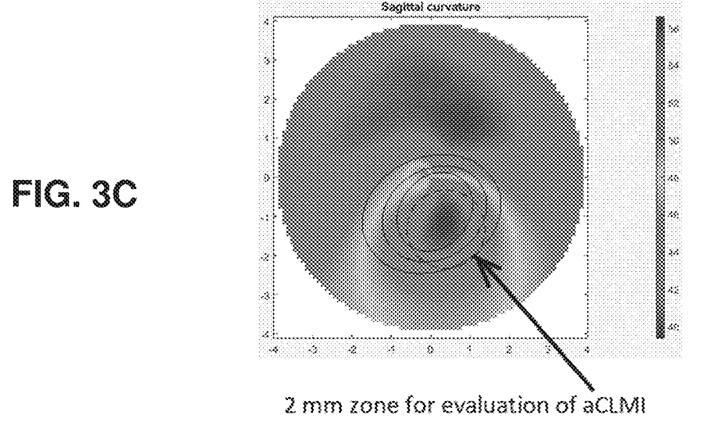
FIG. 3C illustrates an example topography map showing axial (sagittal) curvature.

As shown in FIG. 2, an example automated process 200 for generating optimized treatment patterns generally includes an act 210 where patient-specific tomographic data is received, for example, from a system such as a rotating Scheimpflug camera system (e.g., a PENTACAM® system) or an anterior segment OCT system. The process 200 also includes an act 220 that identifies a location of a keratoconic defect or "cone" using elevation, curvature, or pachymetry data contained in the patient-specific tomographic data. In particular, the patient-specific tomographic data may provide corneal topography maps (either anterior or posterior) indicating the following:
  elevation float (relative to best fit ellipsoid)
  elevation float (relative to reference shape of low order Zernike polynomials) as shown in FIG. 3A
  tangential curvature as shown in FIG. 3B
  axial (sagittal) curvature as shown in FIG. 3C
  pachymetry
Spatial (averaging) filtering may optionally be applied to the conical topography maps to reduce noise.

The act 220 may include an act 220a that generates Zernike coefficients describing the deviation of the corneal surfaces (anterior and/or posterior) from a reference shape. Furthermore, the act 220 may include an act 220b that implements Corneal Location and Magnitude Index (CLMI) analysis, which operates on curvature data and produces estimates for the location of the cone center and cone severity. In particular, the following keratoconus indices may be evaluated:
  axial cone location and magnitude index (aCLMI) and tangential cone location and magnitude index (tCLMI)
    severity terms based on both axial and tangential curvature maps probability of presence of keratoconus
    vertical coma
  other indices based on Zernike decomposition: astigmatism, spherical aberration, total high order aberrations, etc.

The inputs for the Zernike analysis in act 220a may include an elevation map (e.g., from a PENTACAM® system), order of approximation, and normalization diameter. The corresponding outputs may include the Zernike coefficients and a map of elevation residuals relative to a Zernike reference shape. Act 220a may involve Zernike decomposition of the elevation map, with least squares fit of the elevation map by a series of Zernike polynomials and the reference shape including low order terms of the series.

The inputs for the CLMI analysis in act 220b may include axial and tangential curvature maps (e.g., from a PENTA-CAM® system), and the outputs may include the location of cone center, CLMI, and a cone severity term. Act 220b may involve an CLMI algorithm, where for example:

A 2 mm circle is moved over the area of interest.

The cone center is detected at the circle location ($x_0$, $y_0$) where the mean curvature (either axial or tangential) inside the circle reaches its maximum value.

The severity term is the maximum mean curvature above.

CLMI is evaluated from the mean inside and outside curvatures of the 2 mm circle C1 located at cone and the symmetrically located (relative to conical vertex) circle C2.

The same algorithm is used for finding cone center at other maps (pachymetry and elevation residuals).

Additionally, the process 200 includes an act 230 that segments the cone into discrete treatment zones based on predefined geometric parameters. The act 230 may include an act 230a that selects basis data for the segmentation, which may be elevation, curvature, or pachymetry data. The act 230 may also include an act 230b that creates a predefined number of zone boundaries based on the segmentation data. Additionally, the act 230 may include an act 230c that post-processes the boundaries to reduce eccentricity of the treatment shapes, to scale up or down the treatment shapes, and/or to modify zone areas to ensure coverage by a minimum treatment area. In particular, the exposed area around the cone is segmented into several treatment zones using topography maps and different sets of criteria. The innermost zone may be an elliptical area around the cone center; other zones may be bounded by ellipses from both inner and outer sides. Different zones may get different doses of photoactivating light (e.g., UV light). For instance, the doses of photoactivating light may decrease outwardly from the inner zone.

The inputs for act 230 may include a topography map (elevation residuals, curvature, or pachymetry) (e.g., from a PENTACAM® system) selected in act 230a, location of the cone center, the number of zones, processing settings (settings used for the delimitation of zone boundaries), and post-processing settings (settings used for modification of zone boundaries after the processing step is done). The corresponding outputs include a list of elliptic zone boundaries including the following data for each zone: the location of the center of the ellipse, the big and small semi-axes of the ellipse, and tilt angle relative to the nasal-temporal axis. During the delimitation of zone boundaries in act 230b:

1. Depending on the map used, zone boundaries are contours of fixed curvature, elevation float, or conical thickness segmentation variables (SV).
2. The SV values at the innermost and outermost boundaries ($SV_1$ and $SV_{bkg}$) may be evaluated in different ways depending on the processing settings.
3. The SV values at the other boundaries (SW) are evaluated by dividing interval from $SV_{bkg}$ to $SV_1$ into equal parts.
4. Given by the boundary values, $SV_b$, the elliptic boundaries are evaluated as described further herein.

Modification of zone boundaries (post-processing) in act 230c may include the following optional acts order:

1. Reducing eccentricity (innermost and outermost zones only). If the eccentricity of the innermost (outermost) boundary exceeds a predefined limit the big (small) semi-axis is reduced (increased) to reach the limit.
2. Scaling. All zones are scaled up or down keeping their centers fixed.
3. increasing zone areas. If the innermost zone area is below a predefined limit all the zones are scaled up to reach the limit.
4. Replacing outer zone. The outer zone is replaced by the upscaled previous zone.

Segmentation of the inner and outer zones may include the following:

1. Evaluation of the segmentation variable at the cone center—$SV_m$.
2. Evaluation of the background value of the segmentation variable (the value at the outer zone boundary)—$S_{bkg}$. The options include:
   Predefined value (unused for pachymetry and elevation float).
   Mean value over the area of interest.
   Mean value over a circle of predefined diameter centered at vertex.
3. Evaluation of the segmentation variable at the boundary of the innermost zone—$SV_1$. The options include:
   Predefined rise (pachymetry) or drop (others) of segmentation variable relative to $SV_m$.
   Predefined fraction of ($SV_m$-$SV_{bkg}$).
4. Evaluation of segmentation variable at the boundaries of the remaining zones—$S_b$. The remaining drop of the segmentation variable, $SV_1$-$S_{bkg}$ is divided into equal parts.
5. Evaluation of the elliptical zone boundaries (their locations and semi-axes).

Figure 4A:
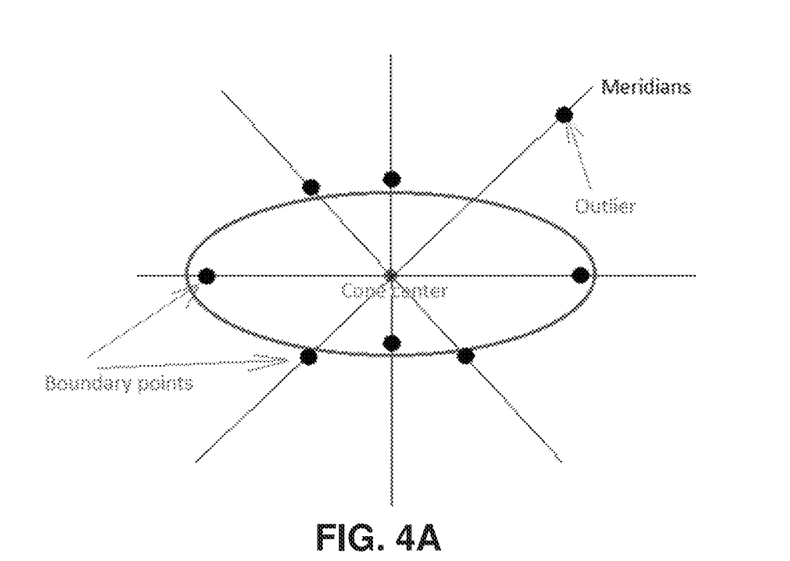
FIG. 4A illustrates aspects of evaluating elliptical zone boundaries for treating eyes with keratoconus.
Figure 4B:
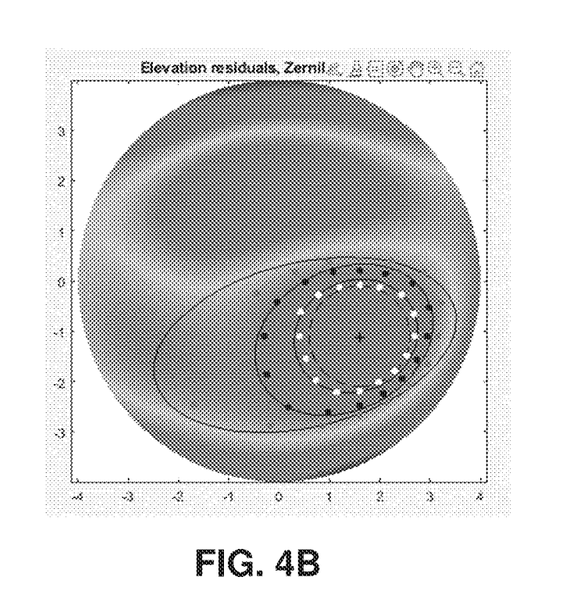
FIG. 4B illustrates aspects of evaluating elliptical zone boundaries for treating eyes with keratoconus.

Referring to FIGS. 4A-B, the evaluation of the elliptical zone boundaries may include:

1. Boundary value, $S_b$, of the segmentation variable is evaluated for each zone boundary, as explained above.
2. A predefined number of meridians is built out of the cone center.
3. For each meridian, a boundary point is found being the 1-st point from the center were segmentation variable rises above (pachymetry) or drops below (others) $S_b$.
4. The elliptical boundary is evaluated as the best fit ellipse to the cloud of the boundary points.
5. Optionally, after the ellipse is calculated the distances of all boundary points to the ellipse are evaluated along the meridians and the outliers are identified and removed.
6. The ellipse is recalculated with the reduced point cloud.
7. The size of the reduced point cloud may be limited from below.

Figure 5A:
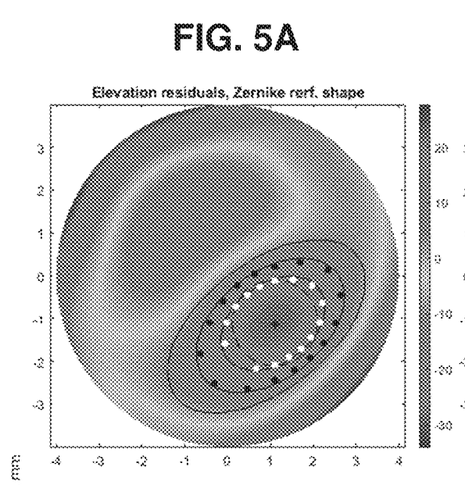
FIG. 5A illustrates example segmentation (without the post-processing) based on an elevation topography map (relative to reference shape of low order Zernike polynomials) as input.
Figure 5B:
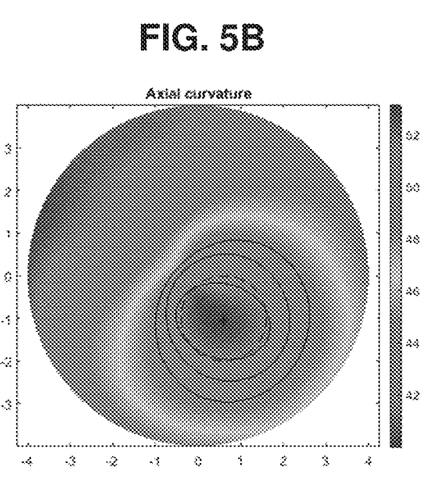
FIG. 5B illustrates example segmentation (without the post-processing) based on an axial curvature topography map as input.
Figure 5C:
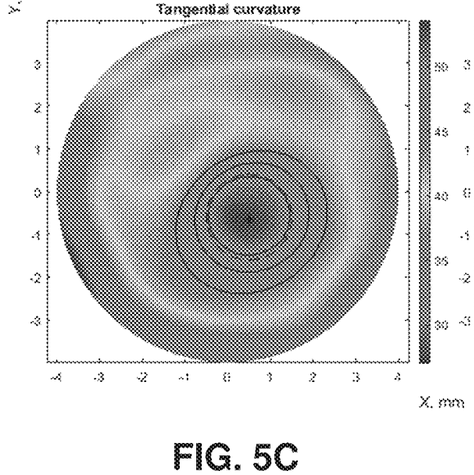
FIG. 5C illustrates example segmentation (without the post-processing) based on a tangential curvature topography map as input.
Figure 5D:
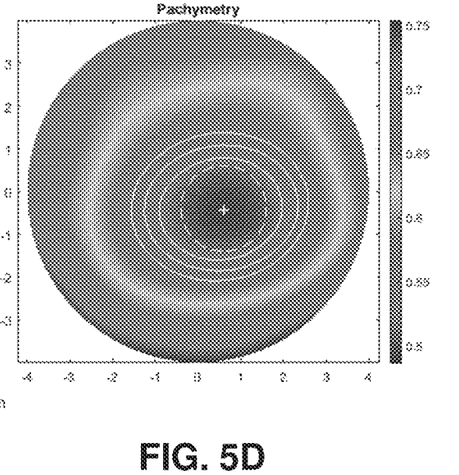

FIGS. 5A-D illustrate examples of segmentation produced by act 230b without the post-processing of act 230c. FIG. 5A corresponds to the processing of an elevation topography map (relative to reference shape of low order Zernike polynomials) as input. FIG. 5B corresponds to the processing of an axial curvature topography map as input. FIG. 5C corresponds to the processing of a tangential curvature topography map as input. FIG. 5D corresponds to the processing of a pachymetry topography map as input.

Figure 6A:
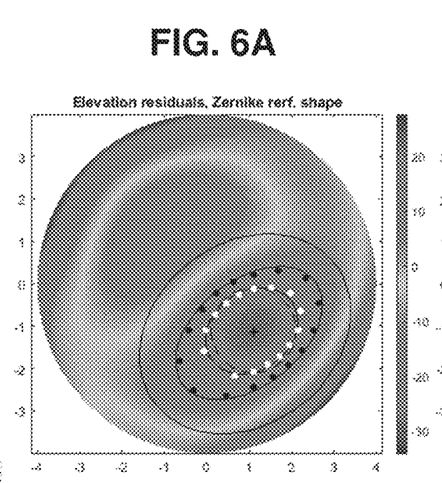
FIG. 6A illustrates example segmentation (with post-processing specifying maximum eccentricity) based on an elevation topography map (relative to reference shape of low order Zernike polynomials) as input.
Figure 6B:
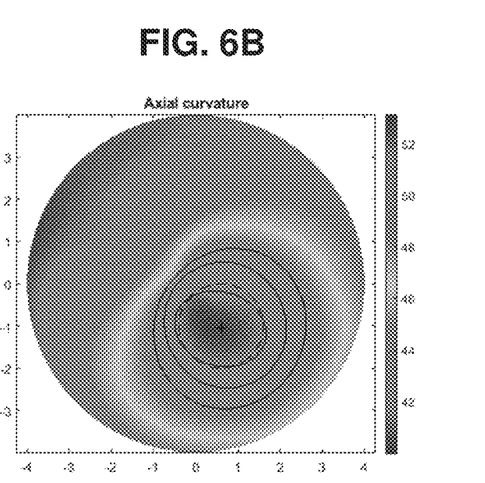
FIG. 6B illustrates example segmentation (with post-processing specifying maximum eccentricity) based on an axial curvature topography map as input.
Figure 6C:
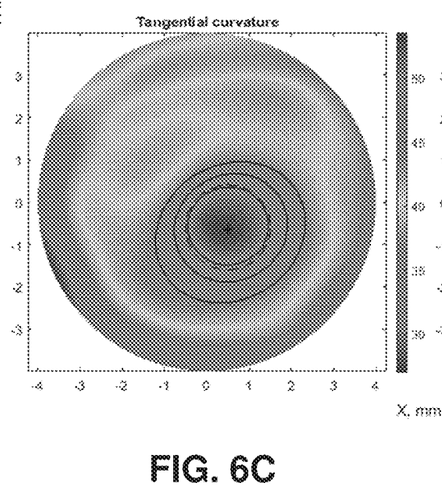
FIG. 6C illustrates example segmentation (with post-processing specifying maximum eccentricity) based on a tangential curvature topography map as input.
Figure 6D:
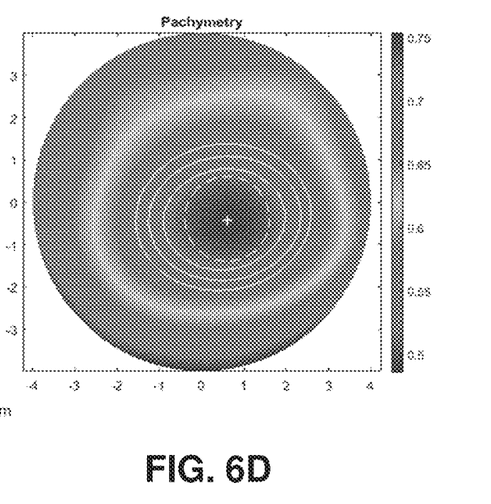

FIGS. 6A-D illustrate examples of segmentation produced by act 230b with the post-processing of act 230c, where the maximum eccentricity is bounded to 0.606. FIG. 6A corresponds to the processing of an elevation topography map (relative to reference shape of low order Zernike polynomials) as input. FIG. 6B corresponds to the processing of an axial curvature topography map as input. FIG. 6C corresponds to the processing of a tangential curvature topography map as input. FIG. 6D corresponds to the processing of a pachymetry topography map as input.

Once an optimized treatment pattern based on the treatment zones is generated, it can be displayed to an operator for confirmation or modification, e.g., prior to implementation by the treatment system 100. Additional features of the process 200 may optionally allow for some degree of user adjustability. For example, the operator can manually input an overall disease severity value (for example, mild, moderate, or severe) that can instruct the process to adapt the size, shape, or UV delivery parameters (irradiance or dose) according to predefined rules. Alternatively, the user can manually input a cone center that can override the automatically determined cone center calculated by the approach above. In response to this input, the treatment pattern can be re-centered according to the user-defined cone center.

In view of the foregoing, systems and methods biomechanically buttress the focally weak region of the stroma and prevent further progression of keratoconus and regularize the cornea to improve visual function of the patient. The principles behind such systems and methods include the following:
 Keratoconus results from focal weakening of the stroma.
 Cross-linking can be spatially applied to regionally stiffen the cornea.
 Selectively stiffening the keratoconus cone leads to greater flattening in the cone region, and compensatory steepening elsewhere: normalization of corneal shape.
 Focal corneal cross-linking patterns generate more shape change than large-diameter patterns because they do not inhibit compensatory steepening outside of the treatment center.

Advantages of such systems and methods include increased potential for improving visual quality in patients with keratoconus, decreased need for physician input to generate treatment patterns, and decreased subjectivity in generation of treatment patterns.

A strategy behind a virtual clinical trial of such systems and methods may include:
 Training a biomechanical finite element analysis (FEA) model using results from customized conical cross-linking treatments from the clinic representing a variety of approaches.
 Creating a treatment pattern process capable of generating focally specific treatments.
 Parameterizing the treatment space and treatment process to generate a variety of responses given the pre-op state of an eye,
 Designing a virtual clinical where each treatment process response forms an arm of the trial and the biomechanical model is used to predict the treatment responses.
 Comparing efficacy of trial arms based on proxies for visual function and the regularization of the keratoconic cornea.

The following parameters may be considered for the virtual clinical trial:
 1. Centration: Vary centration of treatment based on different corneal topographic features.
 anterior curvature (maximum curvature)
 pachymetry (treat point of maximum weakening)
 elevation (posterior or anterior)
 2. Size: scale size of shapes to extend treatment zone relative to cone size
 3. Tapering: Introduce multiple shapes lowering the applied dose in the zones around the a central treatment zone A corresponding treatment process may be created to generate focal treatments of varying centration, size, and tapering.

In an example virtual clinical trial, a cohort of twenty keratoconus eyes were used and a total of twelve treatment arms were used: three centered using an anterior tangential curvature map, three centered using a pachymetry map; three centered using anterior elevation residuals (custom reference surface); and three centered using posterior elevation residuals (custom reference surface). Size and tapering (relative size of central shape) were also varied.

The following performance metrics based on wavefront analysis of the anterior corneal surface may be employed: vertical coma, total astigmatism, spherical aberration, and higher order aberrations (HOA). The average predicted change (reduction) in each of these metrics can be measured for each arm of the virtual clinical trial.

In the example virtual clinical trial, the following results were observed:
 The approaches centered on the posterior and anterior elevation showed the largest reduction in vertical coma, which may be perhaps expected as these treatments are centered on the regions of highest HOA terms which are dominated by vertical coma in many/most eyes.
 The approaches centered on tangential curvature showed a magnitude of change comparable with the posterior elevation centering.
 The larger treatment shapes showed slightly larger reductions in vertical coma.
 The pachymetry based approaches, which are typically more centered, showed the smallest change in vertical coma.
 The approaches centered on the region of lowest pachymetry showed the largest reduction in spherical aberration.
 The approaches centered on tangential curvatures showed a large predicted spread in the change in spherical aberration.
 The approaches centered on elevation showed on average a small increase in spherical aberration.
 The generally central, larger treatments centered on the thinnest pachymetry showed a decrease in total astigmatism.
 The approaches centered on the tangential curvature showed small increases in astigmatism.
 The approaches centered on the posterior and anterior elevation showed a large variation in the predicted change in total astigmatism and are as likely to increase astigmatism as to reduce it.

The following performance metrics based on a topographical changes of the anterior corneal surface may also be employed: Kmax (maximal keratometry (corneal curvature)), Kmax tangential (Kmax-tan), simulated steep keratometry (SimK Steep), aCLMI, tCMLI, and tangential severity term. The average predicted change (reduction) in each of these metrics can be measured for each arm of the virtual clinical trial.

In the example virtual clinical trial, the following results were observed:
 The approaches based on tangential curvature outperformed the other centration options.

Smaller treatment patterns centered on maximum curvature showed the largest predicted change The results for tangential Kmax mirrored the results of sagittal (axial) Kmax.

The approaches based on tangential curvature outperformed the other centration options.

Smaller treatment patterns centered on maximum curvature showed largest change.

The approaches based on Pachymetry (more central) were predicted to have the greater change in SimKs.

The approaches centered on tangential curvature showed a larger spread in the predicted change.

The approaches centered on elevation showed the smallest predicted change in SimKs.

Treatments centered on tangential curvature and thinnest pachymetry showed the most change in the magnitude in the aCLMI.

Treatments centered on elevation residuals showed little average change in aCLMI.

The smaller treatment patterns showed marginally larger changes.

The results for tCLMI were similar to aCLMI.

As described above, according to some aspects of the present disclosure, some or all of the steps of the above-described and illustrated procedures can be automated or guided under the control of a controller. Generally, the controllers may be implemented as a combination of hardware and software elements. The hardware aspects may include combinations of operatively coupled hardware components including microprocessors, logical circuitry, communication/networking ports, digital filters, memory, or logical circuitry. The controller may be adapted to perform operations specified by a computer-executable code, which may be stored on a computer readable medium.

As described above, the controller may be a programmable processing device, such as an external conventional computer or an on-board field programmable gate array (FPGA), application specific integrated circuits (ASIC), or digital signal processor (DSP), that executes software, or stored instructions. In general, physical processors and/or machines employed by embodiments of the present disclosure for any processing or evaluation may include one or more networked or non-networked general purpose computer systems, microprocessors, field programmable gate arrays (FPGA's), application specific integrated circuits (ASIC), digital signal processors (DSP's), micro-controllers, and the like, programmed according to the teachings of the example embodiments of the present disclosure, as is appreciated by those skilled in the computer and software arts. The physical processors and/or machines may be externally networked with the image capture device(s), or may be integrated to reside within the image capture device. Appropriate software can be readily prepared by programmers of ordinary skill based on the teachings of the example embodiments, as is appreciated by those skilled in the software art. In addition, the devices and subsystems of the example embodiments can be implemented by the preparation of application-specific integrated circuits or by interconnecting an appropriate network of conventional component circuits, as is appreciated by those skilled in the electrical art(s). Thus, the example embodiments are not limited to any specific combination of hardware circuitry and/or software.

Stored on any one or on a combination of computer readable media, the example embodiments of the present disclosure may include software for controlling the devices and subsystems of the example embodiments, for driving the devices and subsystems of the example embodiments, for enabling the devices and subsystems of the example embodiments to interact with a human user, and the like. Such software can include, but is not limited to, device drivers, firmware, operating systems, development tools, applications software, and the like. Such computer readable media further can include the computer program product of an embodiment of the present disclosure for performing all or a portion (if processing is distributed) of the processing performed in implementations. Computer code devices of the example embodiments of the present disclosure can include any suitable interpretable or executable code mechanism, including but not limited to scripts, interpretable programs, dynamic link libraries (DLLs), Java classes and applets, complete executable programs, and the like. Moreover, parts of the processing of the example embodiments of the present disclosure can be distributed for better performance, reliability, cost, and the like.

Common forms of computer-readable media may include, for example, a floppy disk, a flexible disk, hard disk, magnetic tape, any other suitable magnetic medium, a CD-ROM, CDRW, DVI), any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

While the present disclosure has been described with reference to one or more particular embodiments, those skilled in the art will recognize that many changes may be made thereto without departing from the spirit and scope of the present disclosure. Each of these embodiments and obvious variations thereof is contemplated as falling within the spirit and scope of the present disclosure. It is also contemplated that additional embodiments according to aspects of the present disclosure may combine any number of features from any of the embodiments described herein.

What is claimed is:

1. A method for treating a cornea having a cone center, comprising:
    receiving tomographic data for a cornea;
    identifying a keratoconic defect in the cornea based on the tomographic data; and,
    segmenting the keratoconic defect into treatment zones based on predefined geometric parameters, wherein the treatment zones indicate where a cross-linking agent is to be applied on the cornea and photoactivated to treat the keratoconic defect,
    wherein segmenting the keratoconic defect into treatment zones includes creating elliptical boundaries for the treatment zones based on segmentation data, wherein the elliptical boundaries are created by evaluating a predefined number of meridians built from the cone center, and
    wherein segmenting the keratoconic defect into treatment zones includes post-processing the boundaries for the treatment zones to at least one of: reduce eccentricity of treatment shapes for the treatment zones, scale up or down treatment shapes for the treatment zones, or modify treatment zone areas.

2. The method of claim 1, further comprising:
    applying the cross-linking agent to the cornea; and
    delivering, with an illumination system, the illumination to photoactivate the cross-linking agent according to the treatment zones.

3. The method of claim 1, further comprising specifying different respective doses of photoactivating light to be delivered to the treatment zones.

4. The method of claim 3, wherein the respective doses of photoactivating light decrease outwardly from an innermost treatment zone.

5. The method of claim 1, wherein the tomographic data provides topography maps showing at least one of elevation, curvature, or pachymetry.

6. The method of claim 1, wherein identifying a keratoconic defect in the cornea based on the tomographic data includes generating Zernike coefficients describing deviation of anterior and/or posterior conical surfaces from a reference shape.

7. The method of claim 1, wherein identifying a keratoconic defect in the cornea based on the tomographic data includes implementing Corneal Location and Magnitude Index (CLMI) analysis to produce estimates for location and severity of the keratoconic defect.

8. The method of claim 1, wherein segmenting the keratoconic defect into treatment zones includes selecting elevation, curvature, or pachymetry data as a basis for segmentation.

9. The method of claim 1, wherein segmenting the keratoconic defect into treatment zones includes creating boundaries for the treatment zones based on segmentation data.

10. The method of claim 1, wherein segmenting the keratoconic defect into treatment zones includes processing boundaries for the treatment zones to at least one of: reduce eccentricity of treatment shapes for the treatment zones, scale up or down treatment shapes for the treatment zones, or modify treatment zone areas.

11. A system for treating a cornea having a cone center, comprising:
- an illumination system configured to deliver illumination that activates a photosensitizing agent applied to a cornea; and
- a controller configured to control the illumination system, the controller including one or more processors and one or more computer readable media, the one or more processors configured to execute instructions from the computer readable media to cause the controller to:
- receive tomographic data for a cornea;
- identify a keratoconic defect in the cornea based on the tomographic data;
- segment the keratoconic defect into treatment zones based on predefined geometric parameters, wherein the treatment zones indicate where a cross-linking agent is to be applied on the cornea and photoactivated to treat the keratoconic defect, wherein the controller segments the keratoconic defect into treatment zones by creating elliptical boundaries for the treatment zones based on segmentation data, wherein the controller segments the keratoconic defect into treatment zones by post-processing the boundaries for the treatment zones to at least one of: reduce eccentricity of treatment shapes for the treatment zones, scale up or down treatment shapes for the treatment zones, or modify treatment zone areas; and
- cause the illumination system to deliver the illumination to photoactivate the cross-linking agent according to the treatment zones,
- wherein the elliptical boundaries are created by evaluating a predefined number of meridians built from the cone center.

12. The system of claim 11, wherein the illumination is ultraviolet (UV) light.

13. The system of claim 11, wherein the instructions from the computer readable media further cause the controller to specify different respective doses of photoactivating light to be delivered to the treatment zones.

14. The system of claim 13, wherein the respective doses of photoactivating light decrease outwardly from an innermost treatment zone.

15. The system of claim 11, wherein the tomographic data provides topography maps showing at least one of elevation, curvature, or pachymetry.

16. The system of claim 11, wherein the controller identifies the keratoconic defect in the cornea by generating Zernike coefficients describing deviation of anterior and/or posterior corneal surfaces from a reference shape.

17. The system of claim 11, wherein the controller identifies the keratoconic defect in the cornea by implementing Corneal Location and Magnitude Index (CLMI) analysis to produce estimates for location and severity of the keratoconic defect.

18. The system of claim 11, wherein the controller segments the keratoconic defect into treatment zones by selecting elevation, curvature, or pachymetry data as a basis for segmentation.

* * * * *